United States Patent
Nance

(10) Patent No.: US 10,406,077 B1
(45) Date of Patent: Sep. 10, 2019

(54) SALIVA COLLECTION APPARATUS

(71) Applicant: Janetta Nance, Nolensville, TN (US)

(72) Inventor: Janetta Nance, Nolensville, TN (US)

( * ) Notice: Subject to any disclaimer, the term of this patent is extended or adjusted under 35 U.S.C. 154(b) by 127 days.

(21) Appl. No.: 15/151,824

(22) Filed: May 11, 2016

(51) Int. Cl.
*A61J 19/00* (2006.01)
*A61M 1/00* (2006.01)

(52) U.S. Cl.
CPC ............ *A61J 19/00* (2013.01); *A61M 1/0019* (2013.01); *A61M 2202/0466* (2013.01); *A61M 2209/088* (2013.01)

(58) Field of Classification Search
CPC .. A61J 19/00; A61J 19/02; A61J 19/04; A61J 19/06; A61M 1/00; A61C 17/00
See application file for complete search history.

(56) References Cited

U.S. PATENT DOCUMENTS

| | | | | |
|---|---|---|---|---|
| 3,067,744 A | * | 12/1962 | Barishman | A61J 19/00 4/258 |
| 3,312,217 A | * | 4/1967 | McKinstry | A61F 5/56 128/848 |
| 4,218,787 A | * | 8/1980 | Puckett | A61J 19/00 4/258 |
| 5,112,322 A | * | 5/1992 | Hathaway | A61J 19/00 128/863 |
| 5,285,940 A | | 2/1994 | Goulter | |
| 6,022,326 A | | 2/2000 | Tatum et al. | |
| 6,158,052 A | | 12/2000 | Smith | |

* cited by examiner

*Primary Examiner* — Tatyana Zalukaeva
*Assistant Examiner* — Gabriella Burnette

(57) ABSTRACT

A saliva collection apparatus including a funnel-shaped saliva collection unit having an upwardly extended substantially trapezoidal lip. A cane-shaped earpiece has a hooked upper portion, a linear middle portion continuously attached to the hooked upper portion, and an L-shaped bottom portion having an upper end and a lower end rotatably and removably attached to an exterior surface of the saliva collection unit. A flexible tube has a top end attached within a funnel opening of the saliva collection unit and a bottom end. A disposable flexible collection bag is removably attached to the bottom end of the tube.

2 Claims, 4 Drawing Sheets

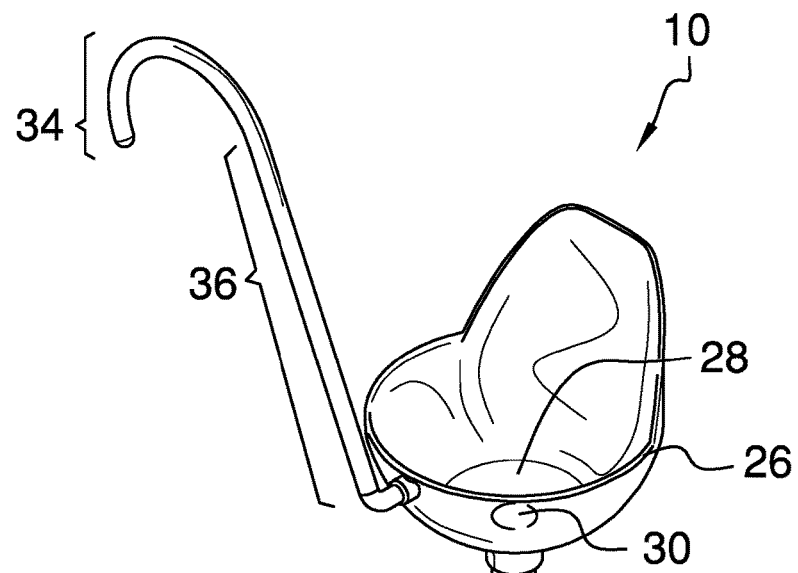
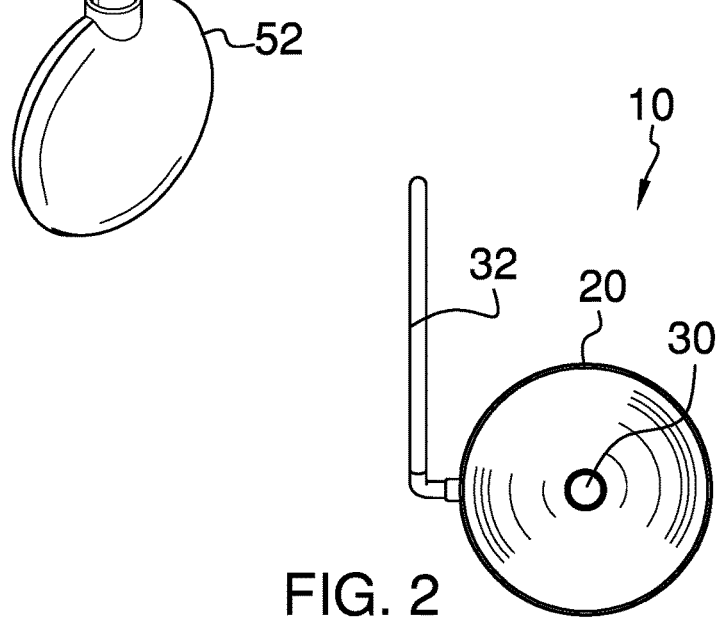

SALIVA COLLECTION APPARATUS

BACKGROUND OF THE INVENTION

Various types of food and liquid collection apparatuses are known in the prior art. However, what has been needed is a saliva collection apparatus including a funnel-shaped saliva collection unit having an upwardly extended substantially trapezoidal lip. What has been further needed is a cane-shaped earpiece having a hooked upper portion, a linear middle portion continuously attached to the hooked upper portion, and an L-shaped bottom portion having an upper end and a lower end rotatably and removably attached to an exterior surface of the saliva collection unit. Lastly, what has been needed is a flexible tube having a top end attached within a funnel opening of the saliva collection unit and a bottom end. A disposable flexible collection bag is removably attached to the bottom end of the tube. The hooked upper portion of the earpiece is configured to be removably disposed around an ear of a user, the collection bag is configured to be removably disposed underneath a chin of the user, and the belt clip is configured to be removably attached to an article of clothing of the user. The saliva collection apparatus thus helps to prevent wet clothes and skin irritation caused by a user's frequent drooling and assists a caretaker in the daily care of the user by eliminating the need to frequently change the user's clothing.

FIELD OF THE INVENTION

The present invention relates to food and liquid collection apparatuses, and more particularly, to a saliva collection apparatus.

SUMMARY OF THE INVENTION

The general purpose of the present saliva collection apparatus, described subsequently in greater detail, is to provide a saliva collection apparatus which has many novel features that result in a saliva collection apparatus which is not anticipated, rendered obvious, suggested, or even implied by prior art, either alone or in combination thereof.

To accomplish this, the present saliva collection apparatus includes a funnel-shaped saliva collection unit having an upwardly extended substantially trapezoidal lip, an exterior surface, an upper edge, a bottom portion, and a funnel opening medially disposed within the bottom portion. A cane-shaped earpiece has a hooked upper portion, a linear middle portion continuously attached to the hooked upper portion, and an L-shaped bottom portion having an upper end and a lower end rotatably and removably attached to the exterior surface of the saliva collection unit proximal the upper edge. The saliva collection unit is removably attachable to the earpiece so that it can be easily removed and cleaned after each use. The middle portion of the earpiece has a bottom end that is rotatably and removably attachable to the upper end of the bottom portion. The middle portion of the earpiece is rotatably attached to the bottom portion of the earpiece so that a user can select whether to attach the hooked upper portion around a front area of his ear or a back area of his ear. A flexible tube has a top end attached within the funnel opening of the saliva collection unit and a bottom end.

The saliva collection apparatus further includes a disposable flexible collection bag, optionally circular, that is removably attached to the bottom end of the tube. The collection bag is removably attachable to the tube so that it can be disposed of and replaced after each use. The collection bag is in fluid communication with the saliva collection unit. It is envisioned that the collection bag will have at least one color coded indicator line to alert the user or a caregiver of the user that the collection bag needs to be changed. A belt clip is attached to the collection bag. The hooked upper portion of the earpiece is removably disposed around an ear of the user, and the collection bag is removably disposed underneath a chin of the user when the earpiece is disposed around the ear of the user. The belt clip is removably attachable to an article of clothing. The tube is sized to extend from proximal the user's mouth to the user's waist, so that the belt clip can optionally attach to a waistband of a pair of pants. The saliva collection unit is preferably egg-shaped and can move from side to side in order to catch drool on either side of the mouth.

Thus has been broadly outlined the more important features of the present saliva collection apparatus so that the detailed description thereof that follows may be better understood and in order that the present contribution to the art may be better appreciated.

BRIEF DESCRIPTION OF THE DRAWINGS

Figures
FIG. 1 is a front isometric view.
FIG. 2 is a top plan view.

DETAILED DESCRIPTION OF THE DRAWINGS

Figure 3:
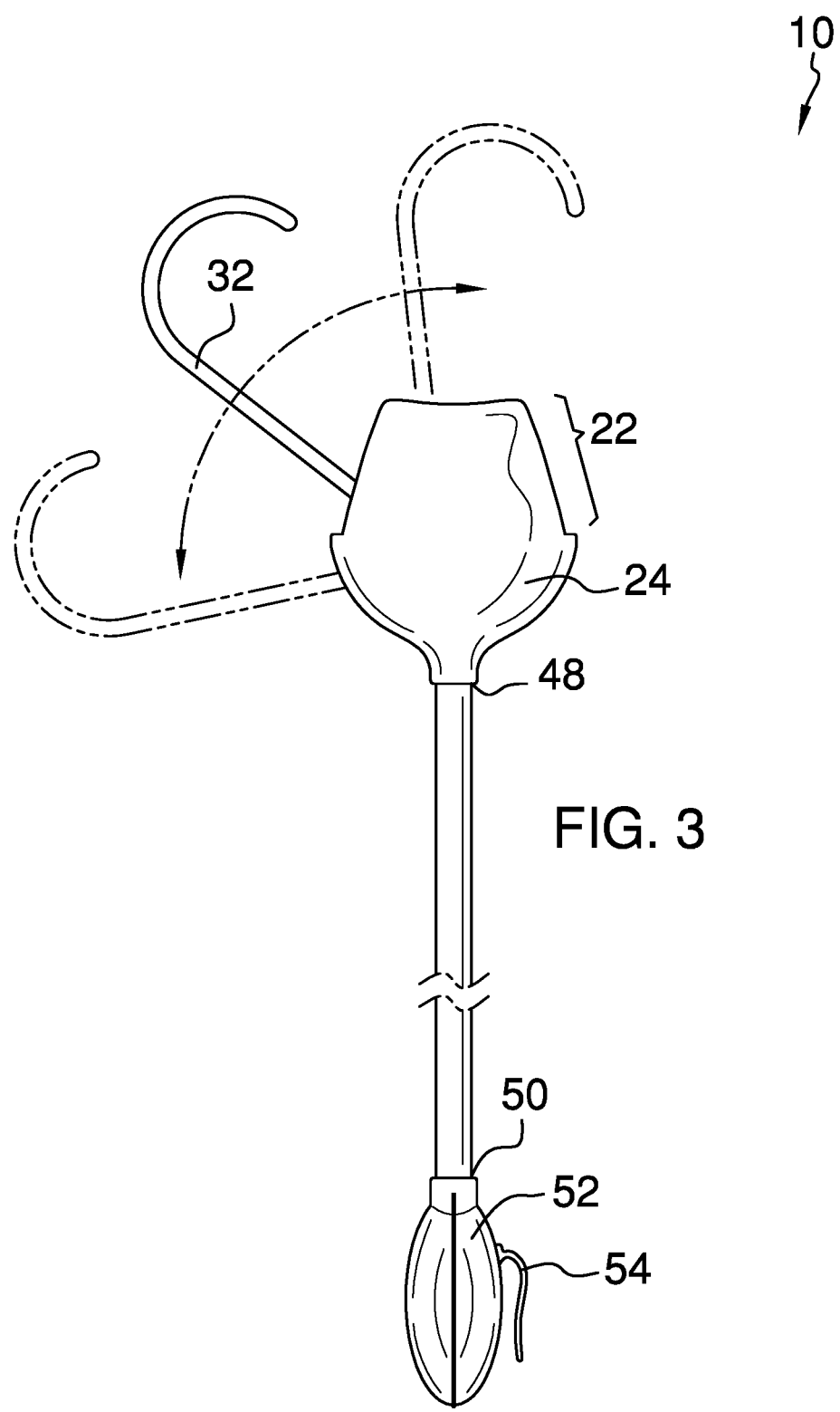
FIG. 3 is a side elevation view.
Figure 4:
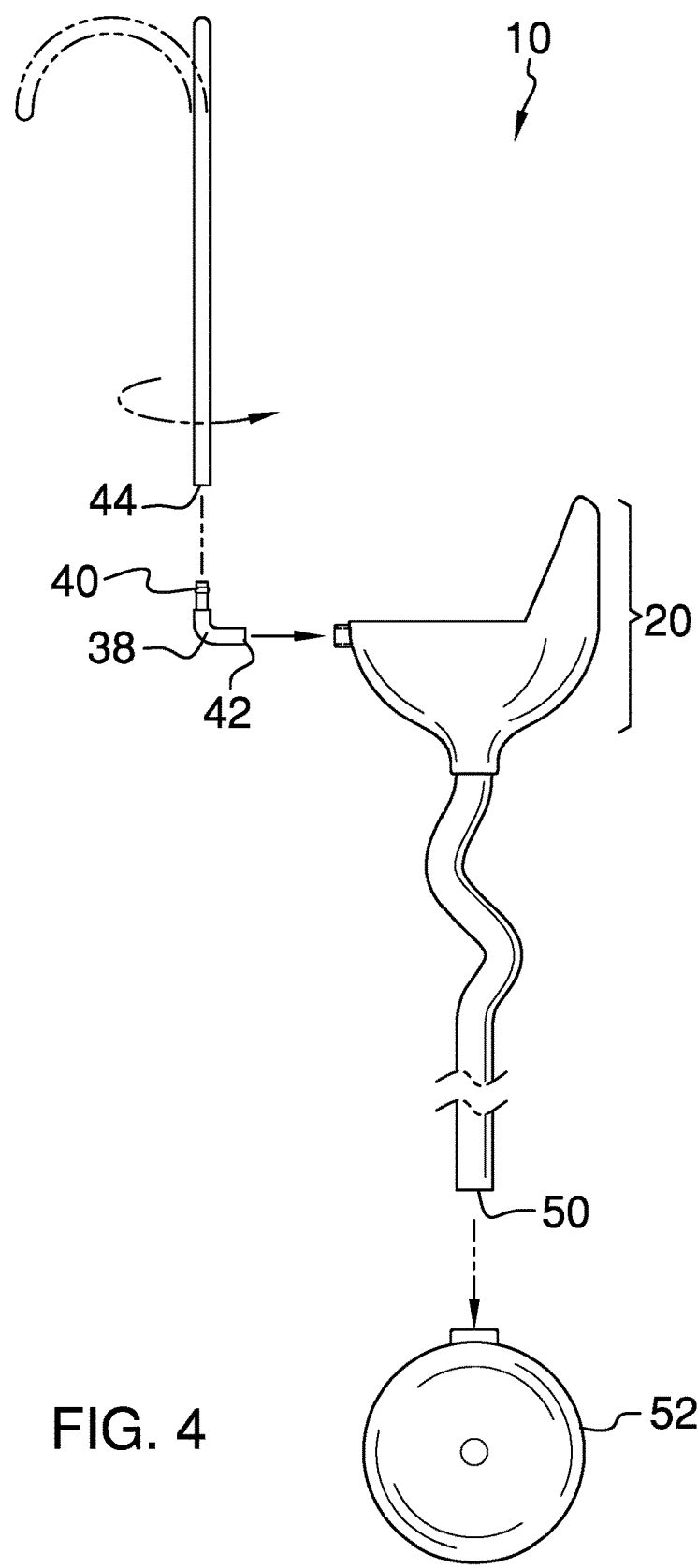
FIG. 4 is a front elevation view.
Figure 5:
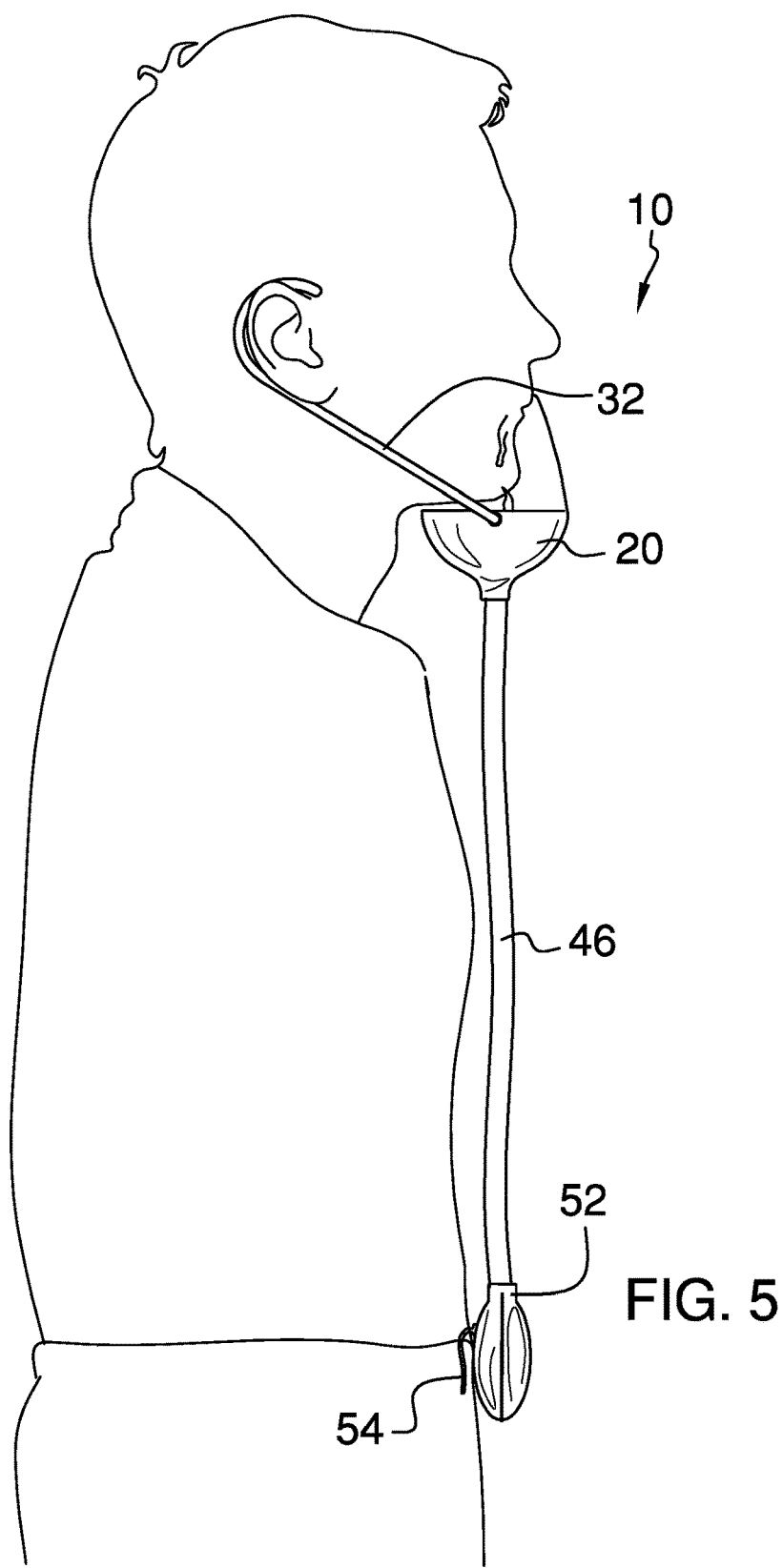
FIG. 5 is an in use view.

With reference now to the drawings, and in particular FIGS. 1 through 5 thereof, an example of the instant saliva collection apparatus employing the principles and concepts of the present saliva collection apparatus and generally designated by the reference number 10 will be described.

Referring to FIGS. 1 through 5 the present saliva collection apparatus 10 is illustrated. The saliva collection apparatus 10 includes a funnel-shaped saliva collection unit 20 having an upwardly extended substantially trapezoidal lip 22, an exterior surface 24, an upper edge 26, a bottom portion 28, and a funnel opening 30 medially disposed within the bottom portion 28. A cane-shaped earpiece 32 has a hooked upper portion 34, a linear middle portion 36 continuously attached to the hooked upper portion 34, and an L-shaped bottom portion 38 having an upper end 40 and a lower end 42 rotatably and removably attached to the exterior surface 24 of the saliva collection unit 20 proximal the upper edge 26. The saliva collection unit 20 is removably attachable to the earpiece 32. The middle portion 36 of the earpiece 32 has a bottom end 44 that is rotatably and removably attachable to the upper end 40 of the bottom portion 38. A flexible tube 46 has a top end 48 attached within the funnel opening 30 of the saliva collection unit 20 and a bottom end 50.

The saliva collection apparatus 10 further includes a disposable flexible collection bag 52, optionally circular, that is removably attached to the bottom end 50 of the tube 46. The collection bag 52 is in fluid communication with the saliva collection unit 20. A belt clip 54 is attached to the collection bag 52. The hooked upper portion 34 of the earpiece 32 is removably disposed around an ear of the user, and the collection bag 52 is removably disposed underneath a chin of the user when the earpiece 32 is disposed around the ear of the user. The belt clip 54 is removably attachable to an article of clothing.

What is claimed is:

1. A saliva collection apparatus comprising:
   a funnel-shaped saliva collection unit having an upwardly extended substantially trapezoidal lip, an exterior surface, an upper edge, a bottom portion, and a funnel opening medially disposed within the bottom portion;
   a cane-shaped earpiece having a hooked upper portion, a linear middle portion continuously attached to the hooked upper portion, and an L-shaped bottom portion having an upper end and a lower end rotatably and removably attached to the exterior surface of the saliva collection unit proximal the upper edge, the middle portion having a bottom end that is rotatably and removably attachable to the upper end of the bottom portion;
   a flexible tube having a top end attached within the funnel opening of the saliva collection unit and a bottom end;
   a disposable flexible collection bag removably attached to the bottom end of the tube, wherein disposable flexible the collection bag is in fluid communication with the saliva collection unit; and
   a belt clip attached to the collection bag;
   wherein the hooked upper portion of the earpiece is removably disposed around an ear of a user;
   wherein the collection bag is removably disposed underneath a chin of the user when the earpiece is disposed around the ear of the user;
   wherein the belt clip is removably attachable to an article of clothing of the user.

2. The saliva collection apparatus of claim 1 wherein the collection bag is substantially circular.

\* \* \* \* \*